US010578535B2

(12) United States Patent
Lazaro Roche et al.

(10) Patent No.: US 10,578,535 B2
(45) Date of Patent: Mar. 3, 2020

(54) METHOD AND DEVICE FOR DETERMINING THE DENSITY OF ROCKY VOLUMES OR ARTIFICIAL BUILDINGS

(71) Applicants: CENTRE NATIONAL DE LA RECHERCHE SCIENTIFIQUE, Paris (FR); UNIVERSITE D'AIX—MARSEILLE, Marseilles (FR); UNIVERSITE NICE—SOPHIA ANTIPOLIS, Nice (FR); UNIVERSITE D'AVIGNON ET DES PAYS DE VAUCLUSE, Avignon (FR)

(72) Inventors: Ignacio Lazaro Roche, Apt (FR); Pierre Elie Marie Salin, Cannes (FR); Stéphane Gaffet, Avignon (FR); Thomas Serre, Marseilles (FR); Jean-Baptiste Decitre, Saint Saturnin les APT (FR); Fanny Catherine Hivert, La Ciotat (FR)

(73) Assignees: UNIVERSITE D'AIX—MARSEILLE, Marseilles (FR); CENTRE NATIONAL DE LA RECHERCHE SCIENTIFIQUE, Paris (FR); UNIVERSITE NICE—SOPHIA ANTIPOLIS, Nice (FR); UNIVERSITE D'AVIGNON ET DES PAYS DE VAUCLUSE, Avignon (FR)

( * ) Notice: Subject to any disclaimer, the term of this patent is extended or adjusted under 35 U.S.C. 154(b) by 0 days.

(21) Appl. No.: 16/099,113

(22) PCT Filed: May 11, 2017

(86) PCT No.: PCT/EP2017/061262
§ 371 (c)(1),
(2) Date: Nov. 5, 2018

(87) PCT Pub. No.: WO2017/194647
PCT Pub. Date: Nov. 16, 2017

(65) Prior Publication Data
US 2019/0212237 A1 Jul. 11, 2019

(30) Foreign Application Priority Data
May 11, 2016 (FR) ...................................... 16 54188

(51) Int. Cl.
*G01N 9/24* (2006.01)
*G01T 1/29* (2006.01)
(Continued)

(52) U.S. Cl.
CPC ............. *G01N 9/24* (2013.01); *G01T 1/2935* (2013.01); *G01T 5/00* (2013.01); *G01T 5/12* (2013.01); *G01V 5/04* (2013.01)

(58) Field of Classification Search
CPC .. H01J 49/00; H01J 49/26; G01N 9/24; G01T 1/2935; G01T 5/12; G01V 5/04
(Continued)

(56) References Cited

U.S. PATENT DOCUMENTS

| 2003/0155519 | A1* | 8/2003 | Francke | ................ G01T 1/2935 250/385.1 |
| 2008/0128604 | A1* | 6/2008 | Bryman | .................. G01T 1/203 250/266 |

(Continued)

FOREIGN PATENT DOCUMENTS

EP    0 081 314 A2    6/1983

OTHER PUBLICATIONS

Gaisser, et al., "Cosmic Rays and Particle Physics", Cambridge, 1990.
(Continued)

*Primary Examiner* — Nicole M Ippolito

(74) *Attorney, Agent, or Firm* — Baker & Hostetler LLP

(57) ABSTRACT

A device for determining the density of volumes of material to be imaged is provided, the device comprising a gas detector having first and second chambers separated by a micro-screen, making it possible to detect a stream of ionising particles, to calculate the path of each ionising particle and the stream of ionising particles passing through the first chamber, and comprising computing means for converting the calculations of paths and streams into information on the volume density of the material to be imaged.

16 Claims, 5 Drawing Sheets

(51) Int. Cl.
 *G01T 5/12* (2006.01)
 *G01V 5/04* (2006.01)
 *G01T 5/00* (2006.01)

(58) Field of Classification Search
 USPC ............. 250/423 R, 242, 427, 306, 307, 288
 See application file for complete search history.

(56) References Cited

U.S. PATENT DOCUMENTS

| 2011/0133071 A1* | 6/2011 | Bashkirov | G01T 1/185 250/282 |
| 2011/0309261 A1* | 12/2011 | Friedman | G01T 1/185 250/382 |
| 2012/0135537 A1* | 5/2012 | Horton | G01N 1/02 436/172 |

OTHER PUBLICATIONS

Bogdanova, et al., "Cosmic muon flux at shallow depths underground", Phys.Atom.Nucl. vol. 69, Issue 8, pp. 1293-1298, Aug. 2006.

Tang, et al., "Muon Simulations for Super-Kamiokande, KamLAND and CHOOZ", Physical Review D, American Physical Society, 74, pp. 053007, Aug. 25, 2006.

Fonte, et al., "Progress in Developing Hybrid RPCs: GEM-like Detectors with Resistive Electrodes", Nuclear Instruments & Methods in Physics Research, Section A, vol. 602, No. 3, pp. 850-853, May 1, 2009.

Brezina, et al., "Operation of a GEM-TPC with pixel readout", IEEE Transactions on Nuclear Science, vol. 59, No. 6, pp. 3221-3228, Dec. 1, 2012.

\* cited by examiner

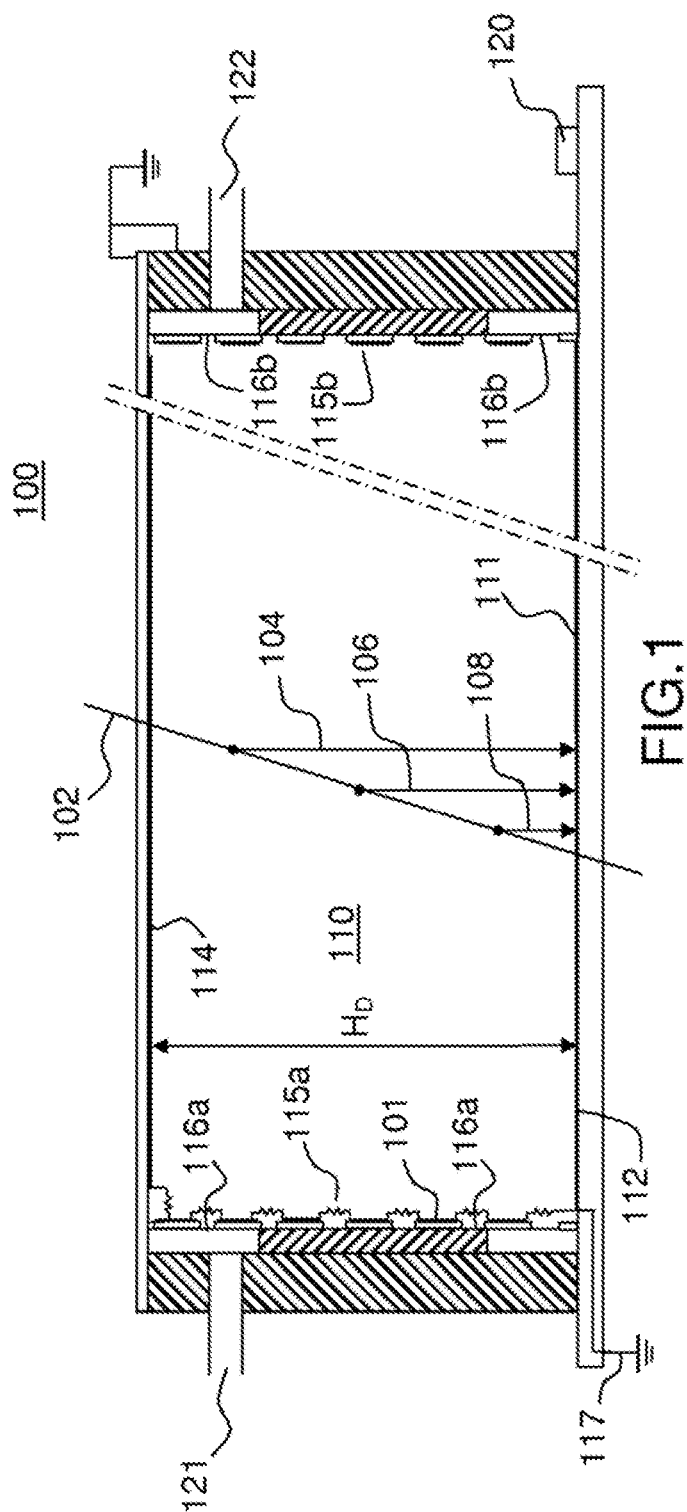
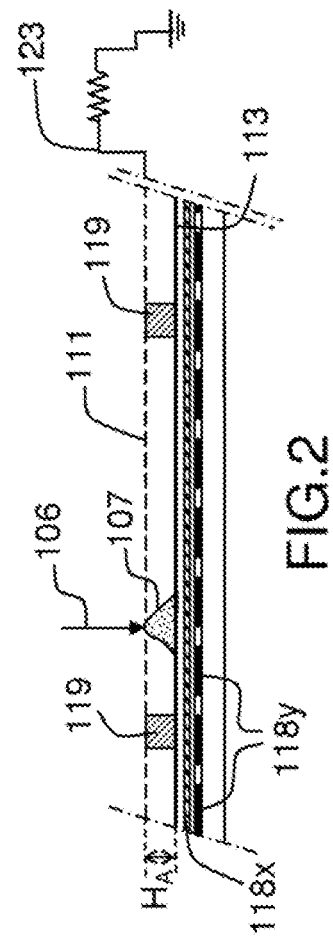

METHOD AND DEVICE FOR DETERMINING THE DENSITY OF ROCKY VOLUMES OR ARTIFICIAL BUILDINGS

CROSS-REFERENCE TO RELATED APPLICATIONS

This application is a National Stage of International patent application PCT/EP2017/061262, filed on May 11, 2017, which claims priority to foreign French patent application No. FR 1654188, filed on May 11, 2016, the disclosures of which are incorporated by reference in their entirety.

FIELD OF THE INVENTION

The invention relates to the field of determining, in transmission, the density of rocky volumes or man-made edifices in situ, and more particularly to a method and a device based on the study of the path and absorption of muons for determining such a density.

BACKGROUND

In geophysics, knowledge of the structure of bedrock and rocks is advantageous in many applications whether with a view to drawing up maps of the bedrock, with the aim of searching for and tracking natural resources for example, to monitoring gravitational instabilities or indeed to monitoring sites the mechanical integrity of which is subject to potential random factors.

The characterization of the properties of bedrock employs indirect measuring techniques such as, for example, seismic imaging, electrical prospection or even gravimetry. Depending on the approach and measuring apparatus used, the obtained data allow, after study and processing, an image of the bedrock to be obtained.

Transmission tomography is a known imaging technique that allows the interior volume of an object (e.g. geological structure, work of art, industrial infrastructure) to be reconstructed on the basis of remote measurements taken from outside of the object.

In patent applications EP 0081314 and US 2008/0128604 A1, a plurality of detectors placed inside a bore well use tomographic analysis to determine local densities, this analysis exploiting electrical signals representative of the path of muons penetrating into the ground and intercepted by the detectors.

Muons are charged particles produced by the interaction of high-energy cosmic protons with the atmosphere. Muons, because of their high mass, which is about 207 times higher than that of electrons, their high speed (0.9997 c) and their insensitivity to the strong interaction, have a high penetrating power with respect to matter. Typically, they will propagate several hundred meters through rock, the depth reached essentially depending on their initial energy and on the density of the medium passed through. Thus, analysis of the number of muons received as a function of path makes it possible to gain information on bedrock density.

Devices such as those of the aforementioned patent applications require a plurality of detectors having a suitable geometry to be installed in order to collect the electrical signals produced by the detectors and to analyze them. Their use however remains limited to zones that have an accessibility that generates few constraints on bulk.

Moreover, it is also necessary to take into account the fact that the number of muons decreases with depth and that at certain depths the low muon flux may require long measurement times. For fluidic detectors, such as that of aforementioned patent application US 2008/0128604 A1, the measurement time is such that variations in the fluid injected into the detector may affect the stability of the measurement. Thus, the quality of the fluid used in a gaseous detector is critical to the achievement of a good system performance.

There is no known solution that allows bedrock density to be characterized from confined environments generating severe bulk constraints while allowing a measurement stability to be achieved. The present invention meets this need.

SUMMARY OF THE INVENTION

One aim of the present invention is to provide a device that allows tomography (or muography) of a medium to the carried out in situ by virtue of the measurement of the flux and of the path of muons passing therethrough. The technique used is nondestructive. It is based on the quantification of the absorption of the natural flux of muons, which depends on the amount of matter that the particles pass through. The absorption rate allows the density of the matter passed through to be deduced, given its geometry.

The implemented method allows bedrock density and variations therein as a function of time to be measured. Using a transmission-based measuring device, the method allows places that are difficult or dangerous to access to be imaged without direct exposure to any risk. The invention allows local variations over time in the density of matter to be monitored.

The present invention has many applications and may, for example, be used to monitor gravitational instabilities, to search for and track natural resources, or even to monitor sites that are subject to natural risks.

Advantageously, the device of the present invention uses a low-bulk gaseous detector combining two chambers that are separated by a micro-grid, namely a first chamber called the drift chamber, which is associated with a second chamber called the amplification chamber, the two chambers together allowing each intercepted muon to be detected and identified.

Generally, the invention is based on the principle of ionization of a gas contained in an enclosure, which is seal-tight to contaminant gases and to dust, comprising two chambers, namely a conversion and drift chamber and an amplification chamber. The passage of a muon through the drift chamber produces electron-positive ion pairs all along its path (about one-hundred ionizations per centimeter). The electric field applied in the drift chamber causes the generated primary electrons to drift over the height of the first chamber, orthogonally to the plane defined by the micro-grid, to the micro-grid, which forms the entrance to the amplification chamber. The signals measured in the amplification chamber will thus trace the projection, onto the plane of the grid, of the initial path of the muon. Counting the paths of the muons allows the local density of the analyzed volume per unit solid angle to be determined. Measurement of the absorption of the muon flux in the bedrock allows the average density of the medium to be mapped for each solid angle given by its azimuth, zenith and elevation.

The invention also relates to a gas-reconditioning system for a gaseous detector, in particular for a gaseous detector such as that claimed in the present invention. Specifically, the performance of gaseous detectors is unavoidably and fundamentally related to the quality and to the stability of the gas used. Conventionally, gaseous detectors operate in an open-circuit mode and generate a loss of a high percentage of gas, limiting their autonomy and degrading their operating environment. To mitigate these drawbacks, a new gas-conditioning system operating in an almost-closed mode is proposed. The provided gas-reconditioning circuit meets the following needs:

the need to decrease as much as possible gas consumption, without decreasing the performance of the detector;

the need to decrease gas emissions, a necessary condition for working in poorly ventilated, confined spaces; and the need to control and stabilize the gain of the detector and the quality of the gas directly in order to acquire then analyze consistent, quality data.

According to one preferred embodiment, the device of the invention is a device for determining the density of volumes of matter to be imaged, which comprises a detector of ionizing particles allowing a flux of ionizing particles to be detected and the path of each ionizing particle through the detector to be calculated, and computing means coupled to the detector in order to convert the calculations of ionizing-particle path into information on the density of the volume of matter to be imaged. The detector is a gaseous detector having a drift first chamber allowing primary electrons to be generated and an amplification second chamber separated from the first chamber by a micro-grid, the device being characterized in that the first chamber comprises first biasing means configured depending on the height of said first chamber to obtain, in the first chamber, a uniform, constant and controlled electric field in order to make the primary electrons drift toward the micro-grid over the height of the first chamber, orthogonally to the plane defined by the micro-grid.

According to one embodiment, the first biasing means are configured to let gas diffuse into the first chamber, in a non-turbulent or convective uniform way.

In one implementation, the first biasing means comprise a printed circuit board comprising interconnected copper tracks and holes allowing the diffusion of the gas.

In one implementation, the computing means are configured to determine the path of each ionizing particle and to calculate the flux of the ionizing particles on the basis of electrical signals produced in the second chamber.

In one implementation, the second chamber comprises second biasing means, allowing an avalanche effect to be produced on the primary electrons passing the micro-grid and secondary electrons to be generated in a micro-avalanche.

According to one embodiment, the ratio between the electric field created in the second chamber and the electric field created in the first chamber is at least higher than 10.

In one implementation, the drift space of the first chamber has a height much larger by several centimeters than the height of the second chamber.

In one implementation, the second chamber has a height of about one-hundred microns.

Advantageously, the gaseous detector placed in or in proximity to a rocky volume allows the volume comprised between the detector and the surface of the ground to be imaged.

In one implementation, the second chamber comprises a resistive protection, either a resistive layer, or a set of resistive tracks producing, by induction, an electric current during the movement of charges in the amplification chamber.

In one implementation, the read tracks located under the resistive protection are superposed and isolated in two different levels along perpendicular axes.

In one embodiment, the device in addition comprises a circuit for injecting gas into the enclosure, said circuit being configured into a circuit that is almost closed between a gas inlet and a gas outlet.

In one implementation, the gas circuit comprises means for filtering out various contaminants present in the gas (e.g. impurities in the initial gas, desorption of constituent materials of the detector, gas depleted by ionization), means for controlling the flow speed of the gas and means for controlling environmental variables.

In one implementation the means for controlling the flow speed of the gas receive measurements of the flow rate of the gas and pressure measurements measured in the gas circuit and temperature information allowing the flow rate of the gas to be adjusted and the gain of the detector to be maintained at a desired value.

The invention also relates to a method for determining the density of volumes of matter to be imaged, the method comprising steps of:

detecting a flux of ionizing particles passing through a detector, said detector being a gaseous detector such as claimed;

calculating the path of each ionizing particle passing through the first chamber of the detector on the basis of primary electrons generated along the path of the ionizing particles passing through said chamber and drifting toward the micro-grid orthogonally to the latter;

calculating the flux of the ionizing particles on the basis of electrical signals amplified in the second chamber, the electrical signals being generated from secondary electrons resulting from an avalanche effect produced on the primary electrons passing the micro-grid; and converting the calculations of path and of flux of the ionizing particles into information on the density of the volume of matter to be imaged.

The invention also covers a computer-program product that comprises code instructions allowing all or some of the steps of the method to be carried out when said program is executed on a computer.

BRIEF DESCRIPTION OF THE DRAWINGS

Various aspects and advantages of the invention will become apparent from the following description of one preferred but nonlimiting implementation of the invention, which description is given with reference to the following figures:

FIG. 1 schematically shows a cross-sectional view of the gaseous detector of the invention according to one embodiment;

FIG. 2 shows a cross-sectional view of a close-up of the amplification chamber of the detector of FIG. 1 according to one embodiment;

DETAILED DESCRIPTION

Figure 3:
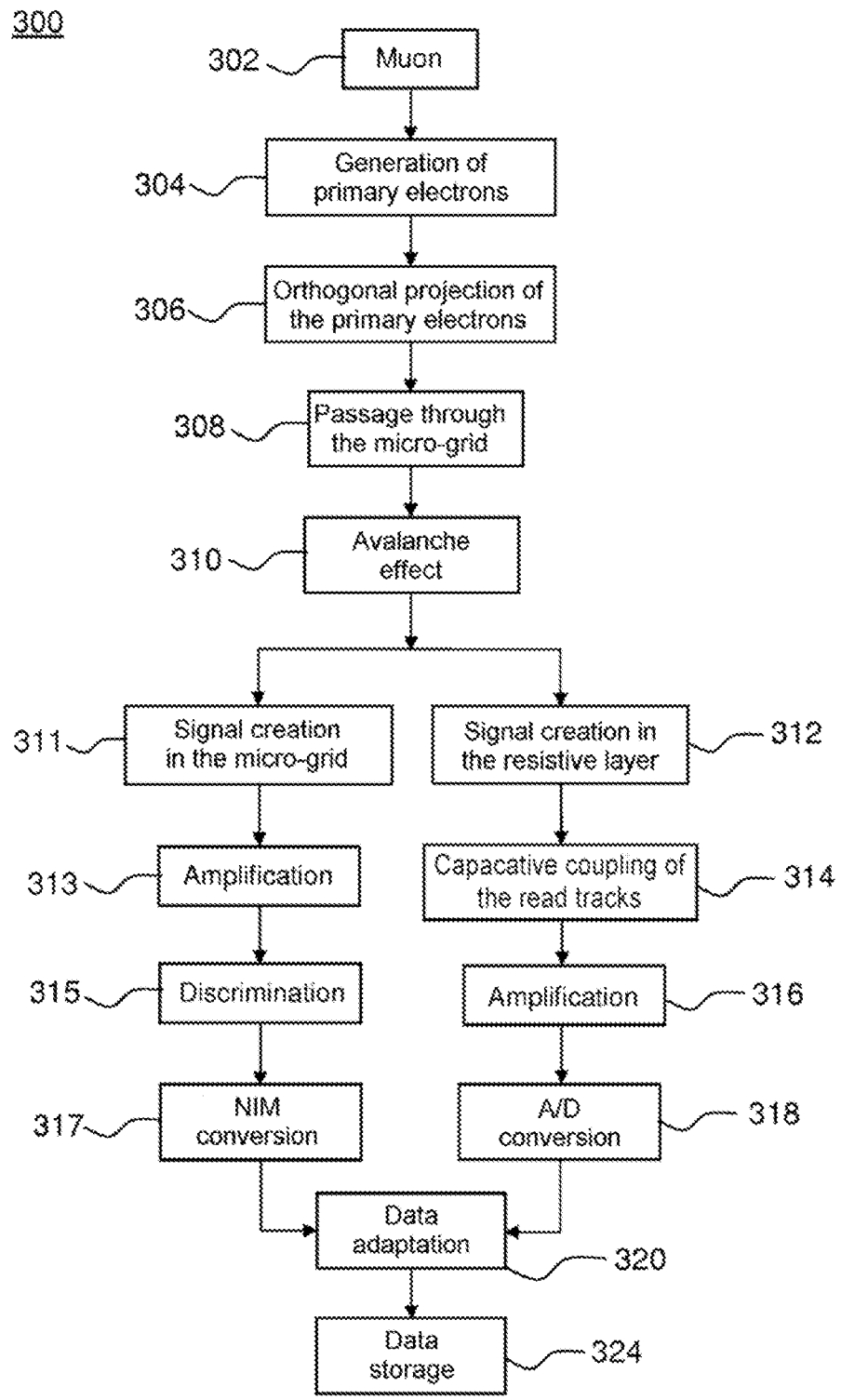
FIG. 3 shows a flowchart of the operating steps of the detector of the invention.

FIG. 1 schematically illustrates a cross-sectional view of the gaseous detector of the invention according to one embodiment.

The gaseous detector (100) of the invention comprises at least a first chamber (110), called the drift chamber (D), which is separated, in the bottom portion thereof, by a micro-grid (111) from a second chamber (112), called the amplification chamber (A), and interfaces (120, 123) with devices for acquiring signals and analyzing and processing data.

The gaseous detector also comprises a gas inlet (121) and a gas outlet (122) with diffusing elements (116a, 116b), allowing a gas to be made to flow into the drift chamber (110). Advantageously, the gas is a gas mixture mainly composed of argon with at least one deactivator, chosen to maximize electron drift speed at the desired electric-field value.

As is detailed below with reference to FIG. 5, the gas injected into the detector originates, in one preferred embodiment, from a gas-reconditioning circuit forming an almost-closed circuit, which has the advantage of filtering, controlling and stabilizing the gain of the gaseous detector of the invention directly, with a view to maximizing its quality and improving the consistency of the data to be analyzed.

The drift chamber in addition comprises a biasing circuit (115a, 115b) coupled between a planar electrode (114), called the drift cathode, which is located in the upper portion of the drift chamber, and ground (117). The cathode located in the upper portion of the primary chamber is placed at a high potential HV1, which allows the biasing circuit to be activated with a view to creating a uniform first electric field in the drift chamber. To generate a cascade of primary electrons from a muon (102) passing through the drift chamber, the biasing circuit creates, in the drift chamber, an electric field that is strong enough to separate the electron-ion pairs formed during the ionization. Because of a predefined configuration of the biasing circuit, the created electric field is uniform and it allows the generated electrons (104, 106, 108) to be projected orthogonally onto the plane of the micro-grid. This point is critical if the measurements required to precisely determine the path of the muons are to be taken.

In order to be able to analyze the path of the muons, the drift chamber of the gaseous detector of the invention has a height '$H_D$' of several centimeters. In one preferred implementation, the distance between the drift cathode (114) and the micro-grid (111) is about 5 cm. Advantageously, the height of the drift chamber is defined so as to obtain a specific precision in the path of the muons and to guarantee a good analysis performance. Thus, the height of the drift chamber must meet two constraints, namely: (1) maximization of the drift space in order to increase the quality of the paths to be determined, and (2) minimization of the volume in order to obtain a compact limited sensor that is suitable for zones that are highly constrained bulkwise.

Unlike known gaseous detectors, such as MicroMegas® detectors, which have a drift chamber (also known as a conversion chamber) of a few millimeters in height, the detector of the invention, because of the unusual height of the drift chamber, creates issues that are not addressed by known detectors. Specifically, the large height of several centimeters of the drift chamber requires particular biasing means to be provided in order to obtain a set and controlled uniform electric field. The shape and features of the biasing system are determined by multi-physics numerical simulations in order to take into account all the complex interactions between processes inside the detector, such as for example diffusion and drift of ions within a fluid, or even the calculation of the paths of charged particles subjected to an electric field. Thus, the biasing system of the invention has a predefined configuration that depends on the height of the drift chamber. The biasing circuit is in one particular implementation produced in the form of a printed circuit board comprising interconnected copper tracks of very high resistances (of about 500 Mohms) and containing small holes in order to let the gas diffuse in a non-turbulent or convective uniform way. Moreover, the biasing circuit serves to minimize the effect of artefacts in the image, in particular on the sides of the detector.

In one preferred implementation, the drift cathode (114) is brought to a negative potential of about −3000 V and the micro-grid (111) is grounded by way of a resistor (121), allowing an electric field of about 500 V/cm to be created in the drift chamber.

FIG. 2 illustrates a cross-sectional view of the amplification chamber (112) of the gaseous detector of FIG. 1. The amplification chamber is defined between the micro-grid (111) and an electrode (113), called the resistive anode, which is a resistive protection. The resistive electrode, which has a set electrical conductivity (0.5-5 MΩ/cm), is composed of a mesh of conductive tracks or strips that are organized according to a predefined template. The primary electrons (106) that pass through the holes in the micro-grid are accelerated until an avalanche effect (107) is created. The arrangement of the strips (x, y) allows a measurable electrical signal to be collected with conventional electronic instrumentation of the signal-acquiring devices (120).

In the detector illustrated in FIGS. 1 and 2, the conductive read strips (118x, 118y) are copper tracks of width that varies depending on how close a track is to the resistive layer, such that the induced electrical signal is as uniform as possible between the various levels. Thus, a track that is close to the resistive anode must have smaller dimensions than a track that is far from this anode. These tracks are protected from sparks by said resistive layer, and distributed along perpendicular 'x' and 'y' axes. This distribution of the conductive tracks allows, via an analysis of the electric pulses induced in these tracks, a position to be determined in two dimensions. In one embodiment, the mesh may for example include 1024 tracks on the 'x' axis and 512 tracks on the 'y' axis.

The conductive strips of the resistive layer are brought to a potential 'HV2' very much lower than the potential 'HV1' of the cathode of the drift chamber. In one preferred implementation, the potential 'HV2' is about 500 V allowing an electric field of about 50 kV/cm to be created in the amplification chamber. The value of HV1 is chosen to optimize the drift speed of the primary electrons. The value of the second field HV2 allows the gain of the detector to be adjusted. However, the two values are not independent because the ratio between the two electric fields affects the number of primary electrons that will be able to pass through the micro-grid toward the second chamber, this also being known as the "electron transparency". A poor electron-transparency value decreases measurement effectiveness.

In addition, the ratio between the electric field created in the second chamber (amplification zone) and the electric field created in the first chamber (drift chamber) depends on the gas used. It is at least higher than 10, and preferably about 50.

The amplification chamber has a height '$H_A$' very much smaller than the height '$H_D$' of the drift chamber. In one preferred implementation, the distance between the micro-grid (111) and the resistive layer (113) is about one-hundred microns.

Pillars (119) are regularly distributed over the surface of the read electrode in order to support the micro-grid, allowing it to be kept at a set distance from the resistive electrode over its entire length. The supporting pillars are made of a dielectric allowing the micro-grid and the resistive layer to be kept electrically insulated and at constant distance. The diameter of the pillars must be as small as possible, in order to limit dead zones in which no detection is possible.

FIG. 3 illustrates the various states of a flux of ionizing particles passing through the detector of the invention. For the sake of simplicity, FIG. 3 illustrates what happens when one particle, such as a muon, passes through the detector, but the principles remain the same for a flux of muons. The principle of the invention is based on the ionization of a gas on the passage of a charged particle (302) through the drift chamber. On its passage, the muon ionizes the gas flowing through the drift chamber and generates what are called primary electrons (304). The generated primary electrons, which are subjected to the electric field that exists in the drift chamber, drift (306) to the micro-grid orthogonally to the latter, the micro-grid being the zone of transition (308) to the amplification chamber. The primary electrons that pass through the holes in the micro-grid are then multiplied by the electric field that exists in the amplification chamber via an avalanche effect (310). The avalanche of what are called secondary electrons and of ions induces a current in the resistive layer (312), this inducing electrical signals (314) in the subjacent conductive read tracks (x, y) via capacitive coupling. The analysis of the signals allows a two-dimensional position (x, y) and an arrival time of the impact associated with the passage of the particle to be determined. All of the electrical signals are then processed by the acquiring and processing circuit (120). The signals are first amplified (316). In one preferred embodiment, the amplifiers are the circuits of a hybrid board of the well-known APV25 type. The analogue signals are subsequently digitized (318) by an analogue/digital converter, then the digital data are adapted (320) and stored (324) in order to be able to be processed by a computer.

The avalanche effect (310) produced in the amplification chamber generates a pulse that is identical but of opposite polarity on the grid (311). The data-analyzing and data-processing device of the detector of the invention allows this signal to be used to provide information on the passage of the ionizing particle through the detector. These induced electrical signals are first amplified (313), then discriminated (315) in order to remove background noise, and then converted into logic pulses (317). In one preferred embodiment, the generated pulses are in the well-known standardized "Nuclear Instrumentation Module" (NIM) format. This NIM pulse serves to trigger the acquisition of data with a view to making it possible to exclusively capture the precise time of the passage of the ionizing particles. This allows the volume of data acquired to be optimized by removing data that are of no interest to the reconstruction of the image. Advantageously, the effectiveness of the detector is improved thereby because data loss related to acquisition with a set sampling frequency for example is minimized (specifically, electronic boards, because of the dead time between samples, are not suitable for recording continuously).

All of the data-acquiring and data-processing circuits may advantageously be located on a single electronic board forming the only interface (120) of the detector of the invention.

In one embodiment (not illustrated) an external data-acquiring device, which is for example scintillator-based, may be added to trigger the acquisition of the data for the analysis of the path of the ionizing particles.

Figure 4:
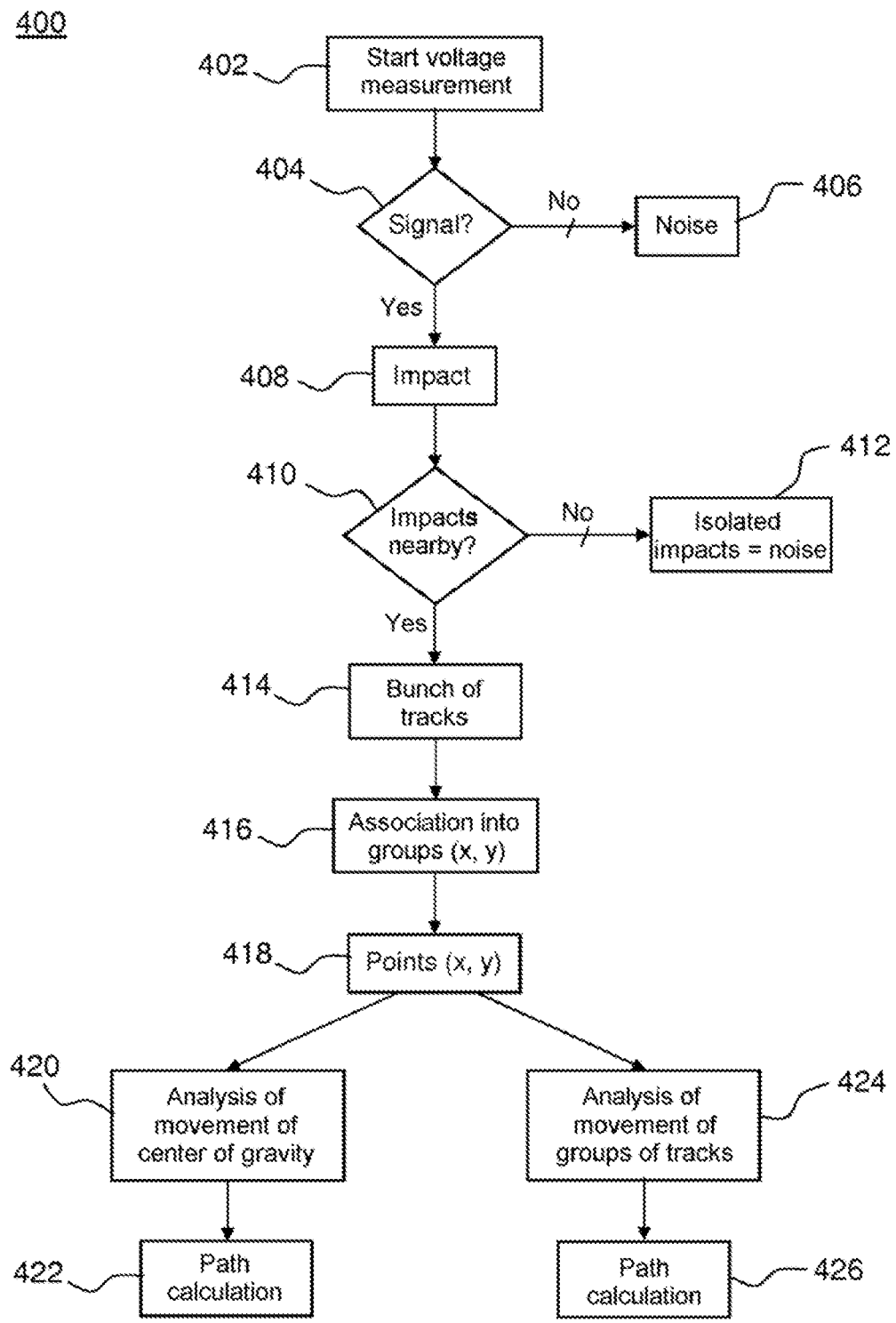
FIG. 4 shows a flowchart of the steps of the data analysis carried out with a view to reconstructing the path of ionizing particles.

FIG. 4 shows a flowchart of the steps of the data analysis carried out with a view to reconstructing the path of the ionizing particles. Unlike the GEM-TPC detector described in the article "Operation of a GEM-TPC with Pixel Readout" by Brezina et al., IEEE Transactions on Nuclear Science, Vol. 59, no. 6, 1 Dec. 2012, which employs a square matrix-array of pixels to determine a 2-D position directly from the position of the irradiated pixel, the principle of the invention is to calculate a precise 2-D position using a combination of irradiated tracks that lie along two axes that are offset by 90°.

The method, which is initiated on the hybrid board (316), which is connected to the interface of the detector (120), starts with the measurement, at regular intervals, of the voltage amplitude of the electrical signals produced in a given period. In one particular implementation, each hybrid board, each of which is dedicated to the measurement of 128 read tracks (x, y), measures voltage every 25 nanoseconds for 67.5 µs.

If the measured voltage is lower than a given threshold (404, NO branch), the measurement is considered to be noise (406). If the measured average voltage is higher than the given threshold (404, YES branch), the measurement is considered to be representative of an impact on a read track and is retained (408). Typically, the threshold is equivalent to the charge on 20,000 electrons.

The method then allows it to be determined whether the impacts noted by each hybrid board are nearby impacts (410) relatively to the read tracks. If the impacts correspond to isolated read tracks, they are considered to be isolated impacts and rejected as noise (412). If the impacts correspond to contiguous read tracks, for example ten contiguous tracks, the method allows the impacted tracks to be grouped (414) along the 'x' axis and along the 'y' axis.

In a following step (416), the method makes it possible to determine which groups of tracks along each axis 'x' and 'y' are impacted in a given time window and to associate them. The association of the groups of tracks (x, y) determines a point (418) providing information on the position of the particle and therefore determines the height at which the particle corresponding to this point passed through the drift chamber, and thus allows its path to be reconstructed. Advantageously, the method allows points to be differentiated depending on the angle of incidence with which the particle penetrated into the drift chamber.

Specifically, for particles that penetrate almost vertically into the detector, the avalanches of secondary electrons in the amplification chamber are very close together, and may overlap. A first processing operation (420) is applied to points for which the angle of incidence with respect to the vertical is almost zero, corresponding to particles that penetrated into the chamber of the detector with an angle of less than 20° (angular range from +10° to −10°). For these particles, all of the groups of nearby tracks are considered to be a single group and the method allows the movement of the center of gravity within this group over the duration of the measurement to be analyzed. The method then allows the azimuthal path of the particle to be reconstructed (422) on the basis of the direction of the movement of the center of gravity and of the positions of the points (x, y).

For particles that penetrate into the detector with a non-zero angle, lying in an angular range comprised between 20° and 90°, a second processing operation (424) is applied. For these particles, the various avalanches of secondary electrons generated during the passage of the particle through the drift chamber, impact groups of tracks that are clearly disassociated and different. The method allows each group of tracks to be analyzed (424) over the duration of the measurement, with a view to determining the variation in the movement of the groups of tracks. The method then allows the azimuthal path of the particle to be reconstructed (426) on the basis of the direction of the movement of the groups of tracks and of the positions of the points (x, y)

In the two preceding cases, once the azimuthal paths are known, the calculation of the path in 3-D is carried out with the obtainment of the zenithal angle of each particle. Knowing the drift speed of the primary and secondary electrons and the journey time (which is given by the separation between electrical signals), the method is capable of reconstructing the vertical distance travelled, and thus the zenithal angle of each path.

Finally, on the basis of the muon flux measured as a function of zenithal and azimuthal angle, it becomes possible to image the density of the medium passed through. Specifically, the attenuation of the muon flux is defined as the ratio between the surface muon flux and the muon flux measured after passage through the medium (e.g. bedrock, work of art, industrial edifice). This parameter is related by a known mathematical relationship to the length of matter passed through multiplied by its average density.

Knowledge of the geometry of the surface of the medium to be imaged allows the length passed through by the muons before they reach the detector to be determined. Those skilled in the art know that the ratio between the number of muons originating from a common origin and the flux is calculated by virtue of measurement, with a detector of set size, of the number of muons and their precise arrival time, this then allowing the muon flux (number of particles per unit area and time) originating from a certain direction to be obtained. The density of an object having known dimensions is proportional to the ratio between the free-sky muon flux and the measured flux, as expressed by the well-known equation: $I/I_0 = \exp(\mu \cdot d)$, where $I_0$ is the surface flux, $\mu$ the density-related attenuation coefficient and d is the distance passed through by the particles. The surface flux $I_0$ is determined by virtue of theoretical models that are able to predict the muon-flux value depending on parameters including altitude, latitude and longitude, such as the following models:

[1] T. K. Gaisser, Cosmic Rays and Particle Physics. Cambridge, 1990
[2] L. N. Bogdanova, M. G. Gavrilov, V. N. Kornoukhov and A. S. Starostin, submitted to Phys. Atom. Nucl. [arXiv: nucl-ex/0601019]
[3] A. Tang, G. Horton-Smith, V. A. Kudryavtsev and A. Tonazzo, submitted to Phys. Rev. E [arXiv:hep-ph/0604078].

Measurement of the flux I then allows the average density 'd' along the path of the particle to be deduced. Thus, measurement of the attenuation of the directional muon flux associated with the topography allows the average density of the medium as a function of azimuth and zenith to be obtained.

Figure 5:
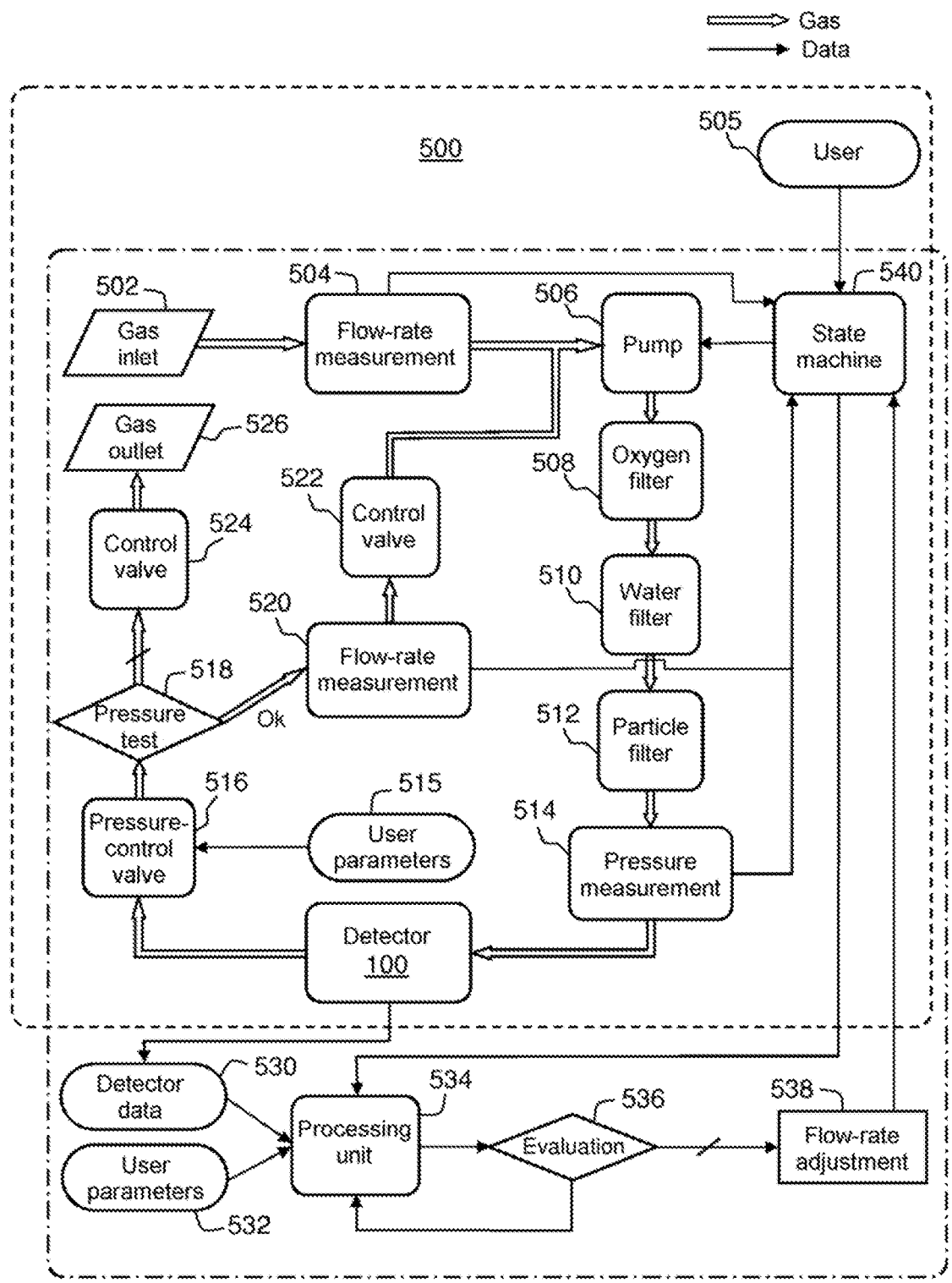
FIG. 5 illustrates the gas and data flows in the gas-reconditioning circuit of the invention.

FIG. 5 illustrates a method for controlling and regulating the distribution and quality of the gas in a gaseous detector. Known gas-distribution circuits for gaseous detectors operate in an open-circuit mode, this generating a substantial loss of gas and a risk of needless pollution of the environment. Moreover, the performance of gaseous detectors depends, inter alia, on the quality and stability of the gas used. A new gaseous-detector gas-distribution device and an associated method are provided. Advantageously, the device is an almost-closed circuit that allows gas consumption to be decreased without decreasing the performance of the detector. The device is composed of a system for filtering out various contaminants present in the gases, which is associated with a circuit for controlling the flow speed of the gas and with a circuit for controlling environmental variables, such as in particular the internal pressure of the gaseous detector and temperature. Advantageously, the combination of the various elements making up the device allows the gain of the gas detector to be controlled and stabilized directly, and thus allows consistent data to be acquired with a view to establishing the trajectory of the particles. Moreover, since the gas-distribution circuit operates in a closed-circuit mode, gas emissions are decreased, this being advantageous and necessary in poorly ventilated confined spaces.

Figure 6:
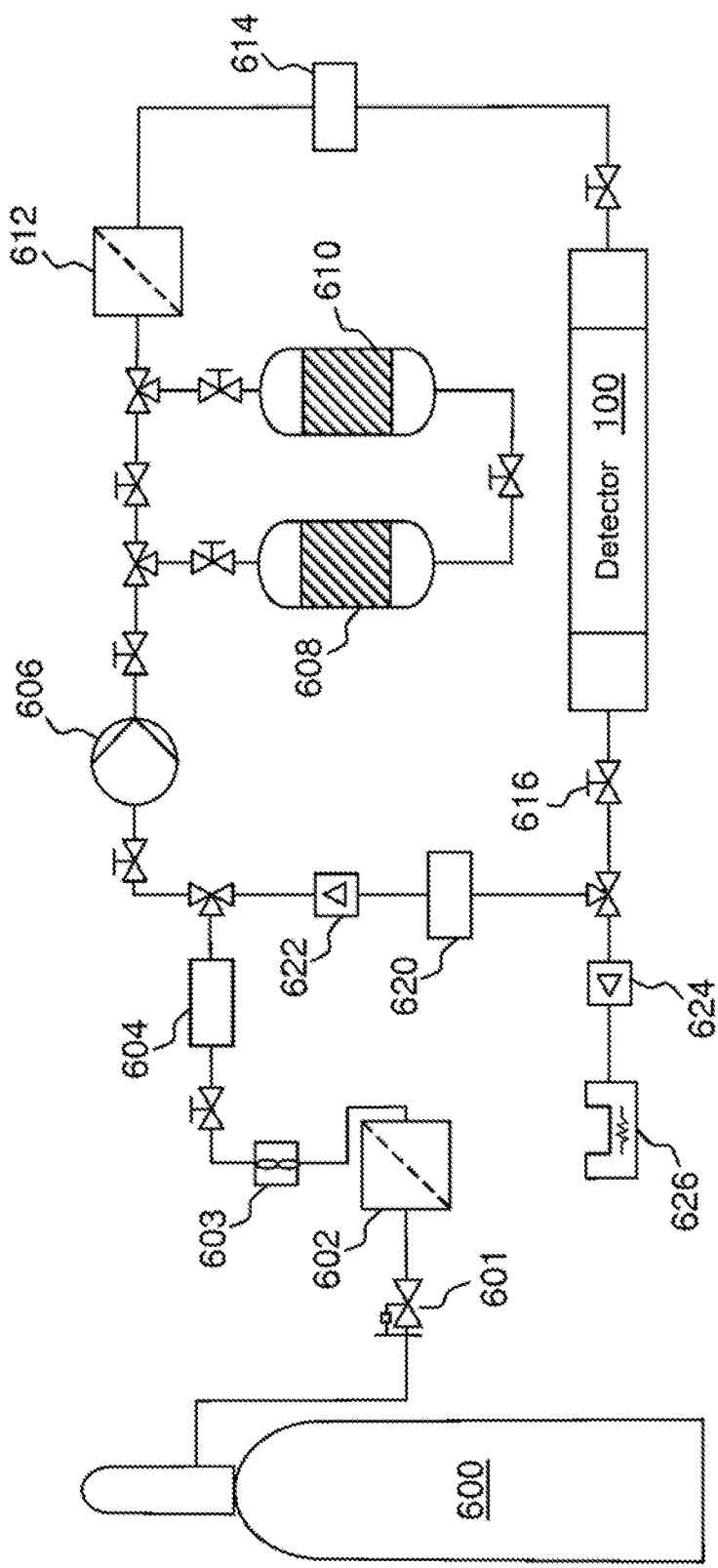
FIG. 6 schematically shows a gas-reconditioning circuit suitable for the detector of the invention according to one embodiment.

FIG. 5 illustrates the gas flow (double arrows) in the closed circuit and the data flow (single arrows) observed at various measurement points in the circuit. FIG. 6 illustrates an implementation of such a gas-distribution device, which implementation is particularly suitable for the gaseous detector of the invention. For the sake of clarity, the data flows are not illustrated in FIG. 6.

The method (500) for controlling and regulating the gas starts with an injection (502) of gas into the inlet of the circuit. As illustrated in FIG. 6, the gas may originate from a high-pressure gas cylinder (600), the gas of which, on exiting the cylinder, passes through a pressure regulator (601) so as to bring the pressure to a defined value, preferably of 0.1 bar maximum above room pressure. The gas is then filtered through a particle filter (602). The filtration allows contamination of the interior of the detector to be avoided by keeping particles in suspension. In a preferred implementation the filter is a 0.22 micron particle filter, 0.22 microns being a value lower than the size of the holes of the micro-grid of the detector. The gas is then fed into the closed-circuit through a variable area flow meter (603) that allows the flow rate of the gas to be controlled manually.

This flow rate is measured digitally (504, 604) at the inlet of the closed circuit and the measurements are transmitted to a PLC (540). The gas is then sent to a variable-speed pump (506, 606) that allows a pressure gradient to be generated in order to force the gas to flow. The gas may then optionally either be filtered in a first filter that retains oxygen (508, 608) followed by a second filter for water vapor (510, 610), or be sent directly to a second particle filter (512, 612), which may be necessary because of impurities freed by the oxygen and water-vapor filters. In a preferred implementation, the particle filter is a 0.22 micron particle filter.

The oxygen filter serves to minimize the absorption of primary electrons by this molecule, thereby increasing the performance of the detector.

The water filter makes it possible to prevent water vapor from reaching the drift chamber, on the one hand for the same reason as the preceding filter, and on the other hand because it greatly decreases the gain of the detector and promotes corrosion thereof.

On exiting the particle filter (512, 612), the pressure of the gas is measured and the values are transmitted to the PLC (510). The gas then enters into the detector (100).

On exiting the detector, an anti-return valve, tared to a desired operating pressure (516, 616) allows the pressure of the gas to be tested (518) with a view to permitting a release of gas and to protecting the system from over pressure. The release is carried out into a bubbler (526, 626) that prevents any entrance of air and allows the exiting gas flow to be seen.

The gas flow exiting the detector (100) is measured (520, 620) allowing the amount of gas in recirculation to be determined. The measured value is transmitted to the PLC (510). The gas then passes to a control valve (522, 622) that allows a return of the gas to be prevented and that forces flow in a single direction.

The gas then passes back to the input pump (506, 606).

The PLC (510) receives measurements of the flow rate of the gas (504, 520) and of the pressure (514) observed in the closed-circuit and temperature information from a thermocouple (527) installed for this purpose, and is capable of adjusting the flow rate of the gas (538).

The circuit for controlling the flow speed of the gas allows the gain of the detector to be maintained at the desired value. The gain of the detector is calculated periodically at adjustable intervals (typically 1 h), using data received (530) from the detector, and is compared with the optimal value designated by the user (532). A processing unit (534) allows the gain of the detector to be determined and this value is compared (536) with a predefined optimum-gain value. In case of a difference between the values, the circuit allows the adjustment (538) to be made to the flow rate to be defined and the value to be transmitted to the PLC (540), which allows the speed of the pump (506) to be automatically modified, thereby adjusting the flow rate of the gas, and allowing the optimum gain value to be returned to.

There is another alternative operating mode that allows the operator to control the PLC (505) manually.

Thus, the proposed gaseous-detector gas-distribution device that operates in a closed-circuit mode combines the effects of filtering of the gas, recirculation of the filtered gas and of direct control of the gain of the detector via measurement and adaptation of operating parameters such as the internal pressure of the detector.

Those skilled in the art will understand that changes may be made to the described preferred implementation while not straying from the principles of the invention.

The invention claimed is:

1. A device for determining the density of volumes of matter to be imaged, comprising a detector of ionizing particles for detecting a flux of ionizing particles and for calculating the path of each ionizing particle through the detector, and comprising computing means coupled to the detector in order to convert the calculations of ionizing-particle path into information on the density of the volume of matter to be imaged, the detector being a gaseous detector having a drift first chamber allowing primary electrons to be generated and an amplification second chamber separated from the first chamber by a micro-grid, the device being wherein the first chamber comprises first biasing means configured depending on the height of said first chamber to obtain, in the first chamber, a uniform, constant and controlled electric field in order to make the primary electrons drift toward the micro-grid over the height of the first chamber, orthogonally to the plane defined by the micro-grid.

2. The device as claimed in claim 1, wherein the first biasing means are in addition configured to let gas diffuse into the first chamber, in a non-turbulent or convective uniform way.

3. The device as claimed in claim 2, wherein the first biasing means comprise a printed circuit board comprising interconnected copper tracks and holes allowing the diffusion of the gas.

4. The device as claimed in claim 1, wherein the computing means are configured to determine the path of each ionizing particle and to calculate the flux of the ionizing particles on the basis of electrical signals produced in the second chamber.

5. The device as claimed in claim 1, wherein the second chamber comprises second biasing means allowing a second electric field to be generated in the second chamber, allowing an avalanche effect to be produced on the primary electrons passing the micro-grid and secondary electrons to be generated in a micro-avalanche.

6. The device as claimed in claim 1, wherein the ratio between the electric field created in the second chamber and the electric field created in the first chamber is at least higher than 10.

7. The device as claimed in claim 1, wherein the drift space of the first chamber has a height much larger by several centimeters than the height of the second chamber.

8. The device as claimed in claim 1, wherein the second chamber has a height of about one-hundred microns.

9. The device as claimed in claim 1, wherein the gaseous detector is placed in or in proximity to said volume of matter to be imaged.

10. The device as claimed in claim 1, wherein the electrically conductive read tracks are protected by a resistive layer producing, by induction, an electric current during the movement of charges in the second chamber.

11. The device as claimed in claim 10, wherein the read tracks under the resistive protective layer are superposed and isolated in two different levels along perpendicular axes.

12. The device as claimed in claim 1, further comprising a circuit for injecting gas into the detector, said circuit being configured into a circuit that is almost closed between a gas inlet and a gas outlet.

13. The device as claimed in claim 12, wherein the gas circuit comprises means for filtering out various contaminants present in the gas, means for controlling the flow speed of the gas and means for controlling environmental variables.

14. The device as claimed in claim 13, wherein the means for controlling the flow speed of the gas receive measurements of the flow rate of the gas and pressure measurements measured in the gas circuit and temperature information allowing the flow rate of the gas to be adjusted and the gain of the detector to be maintained at a desired value.

15. A method for determining the density of volumes of matter to be imaged comprising:
detecting a flux of ionizing particles passing through a detector, said detector being a gaseous detector according to claim 1;
calculating the path of each ionizing particle passing through the first chamber of the detector on the basis of primary electrons generated along the path of the ionizing particles passing through said chamber and drifting toward the micro-grid orthogonally to the latter;
calculating the flux of the ionizing particles on the basis of electrical signals amplified in the second chamber, the electrical signals being generated from secondary electrons resulting from an avalanche effect produced on the primary electrons passing the micro-grid; and
converting the calculations of path and of flux of the ionizing particles into information on the density of the volume of matter to be imaged.

16. A computer-program product, said computer program comprising non-transitory code instructions allowing to carry out the steps of the method according to claim 15, when said program is executed on a computer.

* * * * *